United States Patent [19]

Yamada

[11] Patent Number: 5,254,006
[45] Date of Patent: Oct. 19, 1993

[54] PERMANENT MAGNET ASSEMBLY FOR FALSE TOOTH STABILIZATION

[75] Inventor: Hirohide Yamada, Saitama, Japan

[73] Assignee: Hitachi Metals, Ltd., Tokyo, Japan

[21] Appl. No.: 943,557

[22] Filed: Sep. 11, 1992

[30] Foreign Application Priority Data

Sep. 12, 1991 [JP] Japan .................. 3-232129

[51] Int. Cl.$^5$ .......................... A61C 13/235
[52] U.S. Cl. .................................. 433/189
[58] Field of Search ................ 433/189, 172

[56] References Cited

U.S. PATENT DOCUMENTS

| | | | |
|---|---|---|---|
| 4,431,419 | 2/1984 | Portnoy | 433/189 |
| 4,815,975 | 3/1989 | Garrel et al. | 433/189 |
| 4,857,873 | 8/1989 | Gillings | 433/189 X |
| 4,911,640 | 3/1990 | Schwab | 433/189 |
| 5,013,243 | 5/1991 | Tanaka et al. | 433/189 |
| 5,123,843 | 6/1992 | Van der Zel et al. | 433/189 |

FOREIGN PATENT DOCUMENTS

| | | | |
|---|---|---|---|
| 3140464 | 4/1983 | Fed. Rep. of Germany | 433/189 |
| 4-227253 | 8/1992 | Japan . | |

OTHER PUBLICATIONS

Jackson, "The Application of Rare Earth Magnetic Retention to Osseointegrated Implants", Oral Maxillo-Facial Implant, vol. 1, No. 2, 1986.

Primary Examiner—Gene Mancene
Assistant Examiner—Nicholas D. Lucchesi
Attorney, Agent, or Firm—Finnegan, Henderson, Farabow, Garrett & Dunner

[57] ABSTRACT

A permanent magnet assembly for false tooth stabilization which includes a cup-shaped case formed of a corrosion resistant and magnetic material, an axially magnetized permanent magnet stored in the case, and a seal plate formed of a corrosion resistant material and fitted into and fixed to an end opening in the case to hermetically seal the case, the seal plate being composed of a central seal plate portion formed of a magnetic material to face the end face of the permanent magnet and a seal edge portion formed of a non-magnetic material to face in the region of the outer periphery of the permanent magnet. The width dimension of the seal edge portion is in the range of 0.03 to 0.07 mm, and at least the abutting portions of the case and seal plate are welded to each other.

8 Claims, 2 Drawing Sheets

WIDTH DIMENSION t OF THE SEAL EDGE MEMBER (mm)

PRIOR ART

PERMANENT MAGNET ASSEMBLY FOR FALSE TOOTH STABILIZATION

BACKGROUND OF THE INVENTION

1. Field of the Invention

The present invention relates to permanent magnet assemblies for false tooth stabilization which can be used for holding a false tooth by magnetic attraction provided by a permanent magnet.

2. Description of the Related Art

Various attempts have been made to use magnetic attraction acting between a permanent magnet and a soft magnetic alloy for fixing a false tooth into the oral cavity. For example, techniques representing such attempts are described in "The Application of Rare Earth Magnetic Retention to Osseointegrated Implants, Oral Maxillo-Facial Implant", Vol. 1 (1987), No. 2, pages 77 to 89, by T. R. Jackson.

In order to place the above-mentioned type of false tooth, several conditions are required. For example, one of the conditions is that the permanent magnet be completely hermetically sealed in a case formed of a material which is harmless to a human body. Another condition is that the permanent magnet have a small magnetic flux leakage to the outside.

An example of a conventionally used permanent magnet assembly which has such a structure is shown in FIGS. 5(a) and 5(b). FIG. 5(a) is a perspective view of the permanent magnet assembly, showing the outer appearance thereof and FIG. 5(b) is a diametric cross section of the permanent magnet assembly. As shown in FIGS. 5(a) and 5(b), a permanent magnet 1, which is formed of a rare earth cobalt material or the like, in a cylindrical shape, and which is also magnetized in an axial direction shown by an arrow in FIG. 5(b), is stored in a case 2 formed of stainless steel, having magnetic and high corrosion resistance and also which has a U-shaped cross section to define an overall cup-shaped configuration. The case 2 is covered and hermetically sealed by a thin disc cover plate 3 which is formed of non-magnetic stainless steel having a high corrosion resistance. These components are then bonded together by use of an adhesive agent 4, thereby to provide a permanent magnet assembly 10 which has a closed structure.

FIG. 6 is a cross sectional view of main portions of false tooth fixing means which uses a conventional permanent magnet assembly. In FIG. 6, a root surface member 7, which is formed of a soft magnetic alloy with a T-shaped longitudinal section, is embedded in an alveolus 9. A dental plate 8 is shown in which a permanent magnet assembly 10 shown FIG. 5 is to be embedded in such a manner that a portion thereof located on the side of the cover plate 3 is opposed to the root surface member 7. This structure allows magnetic attraction to act between the permanent magnet assembly 10 and root surface member 7. The magnetic attraction pulls the dental plate 8 against the alveolus 9, so that the dental plate 8 can be stabilized in the mouth.

In this case, the magnetic flux from the permanent magnet 1 passes through a magnetic path including the root surface member 7, the case 2, and the permanent magnet 1, and, therefore, magnetic flux leakage to the outside is very small. Also, because the case 2 and cover plate 3 are both made of stainless steel, they have sufficient corrosion resistance and wear resistance against the biting force of the false tooth 11. Further, the adhesive agent 4 is also said to have sufficient adhesive strength, air tightness when it is used in the oral cavity, and chemical stability.

However, the conventional permanent magnet assembly 10 constructed in the above-mentioned manner has several problems to be solved. For example, although the adhesive agent 4 used to bond the respective components of the assembly 10 together is said to have a sufficient adhesive property, because it is formed of an organic compound, when used for a long time, the adhesive agent 4 is not likely to maintain its chemical stability nor its adhesive strength. For this reason, a permanent magnet assembly of a closed type having a higher reliability is required. Also, while the magnetic circuit of the above-mentioned conventional permanent magnet assembly 10 minimizes leakage of magnetic flux, it suffers from a reduction in the magnetic attracting force that is a most important property. Therefore, a permanent magnet assembly which has a greater attracting force and is thus able to hold a false tooth in a stable manner is needed.

In order to solve the above-mentioned problems, the present applicants have previously filed patent applications (Japanese Patent Application Nos. 2-157285 and 3-141691 of Heisei), each of which relates to a permanent magnet assembly for false tooth stabilization, comprising a permanent magnet, a case formed of a corrosion resistant and magnetic material having a recessed portion for storing the permanent magnet, and a seal plate formed of a corrosion resistant material for covering the case to prevent the permanent magnet from being exposed from an opening of the case recess. The seal plate is formed with a seal edge member of a corrosion resistant and non-magnetic material and a central seal plate member formed of a corrosion resistant and soft magnetic material. The central seal plate member has an outer peripheral shape substantially the same as the inner peripheral shape of the seal edge member. Also, the case and seal plate are welded to each other in the respective abutting portions thereof.

According to the above invention, the permanent magnet 1 can be closed completely without exposing the adhesive agent 4 as shown in FIG. 5 to the outer peripheral surface of the permanent magnet assembly 10 or without using any adhesive agent 4 and, for this reason, reliability in the closure is enhanced. Also, since a magnetic air gap between the permanent magnet 1 and root surface member 7 shown in FIG. 6 is minimized, the attraction can be increased and the degree of resistance to wear can be improved. However, in recent years, a higher degree of performance has been required of the permanent magnet assembly 10 of this type as well as stronger magnetic attraction.

Also, according to the permanent magnet assembly for false tooth stabilization proposed by the above-mentioned Japanese Patent Applications Nos. 2-157285 of Heisei and 3-141691 of Heisei, the abutting portions of the case and seal plate as well as the abutting portions of the seal edge member and central seal plate member are welded to each other by a laser. However, when the case and seal plate are laser welded to each other in the abutting portions thereof, they are distorted due to heat generated in welding and thus subject to air gaps or undulations between the abutting portions of the seal edge portion and seal plate member. This causes unwanted dimensional variation of the permanent magnet assembly.

SUMMARY OF THE INVENTION

The present invention has been made in view of the above circumstances and has as an object to provide a permanent magnet assembly for false tooth stabilization which is improved in reliability and is greatly increased in magnetic attraction.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, there is provided a permanent magnet assembly for false tooth stabilization comprising a cup-shaped case having an opening, the case being formed of a corrosion resistant and magnetic material, a permanent magnet having opposite end faces, magnetized in the direction between the end faces thereof and positioned in the case, and a seal plate formed of a corrosion resistant material and fitted into and fixed to the opening of the case to hermetically seal the case, said seal plate comprising a central seal plate portion formed of a magnetic material and facing an end face of said permanent magnet, and a seal edge portion formed of a non-magnetic material to face the region of the outer peripheral edges of said permanent magnet, the radial width dimension of said seal edge portion being in the range of 0.03 to 0.07 mm, and at least the abutting portions of said case and said seal plate being welded to each other.

According to the invention, if the width dimension of the seal edge portion is less than 0.03 mm, then a magnetic air gap between the seal plate member and case becomes so small that a magnetic flux contributing to the magnetic attraction is not able to act on the root surface member. Also, if the width dimension of the seal edge portion is greater than 0.07 mm, then the magnetic attraction is unfavorably decreased. In the present invention, the maximum value of the magnetic attraction can be obtained when the width dimension of the seal edge portion is on the order of 0.05 mm. However, in order to keep variations in the magnetic attraction of the permanent magnet assembly within ±3% of the above mentioned maximum value, the width dimension of the seal edge portion is defined to be in the range of 0.03 to 0.07 mm.

To seal the permanent magnet assembly with the metal materials of the case and seal plate, although brazing, soldering and the like are available, according to the invention, welding is especially preferable. For example, spot welding by use of a laser beam may be repeated at sufficiently small spacing increments to effect a continuous weld. This technique is advantageous partly because it avoids deterioration of the magnetic strength of the permanent magnet being hermetically sealed, partly because the sealing must use only metals that have been proved harmless to a human body and partly because of the dimensional precision of the assembly. As mentioned above, according to the invention, since the width dimension of the seal edge portion is limited to the range of 0.03 to 0.07 mm, if the components of the present permanent magnet assembly are laser welded to develop a bead width of from 0.15 to 0.20 mm and a bead depth of from 0.15 to 0.20 mm, then the abutting portions of the case and seal plate as well as the abutting portions of the seal edge portion and central seal plate portion are welded simultaneously, thereby avoiding a requirement for two laser welding operations of the conventional permanent magnet assembly.

Also, the permanent magnet to be used in the present invention must be compact and provide a magnetic flux as strong as possible. For this reason, a rare earth magnet such as a Sm - Co system magnet, a Nd Fe system magnet, or the like, is used. Also, the shape of the permanent magnet may generally be cylindrical to conform with the space in which the permanent magnet is normally used. Therefore, in most cases, a ring-shaped thin member is used for the seal edge portion and a disc-shaped thin member is used for the central seal plate portion. Further, the permanent magnet is normally magnetized before it is put into the case. However, the permanent magnet may be magnetized after the permanent magnet assembly has been assembled.

Because of the above-mentioned structure, magnetic flux from the permanent magnet can readily reach the surface of the seal plate member to increase the magnetic attraction between the seal plate member and the root surface member opposed to the seal plate member. Also, because the seal edge portion formed of a non-magnetic material is interposed between the central seal plate portion and the case, a short circuit is prevented between the seal plate member and the case, thus contributing to increased magnetic attraction.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENT

Figure 1:
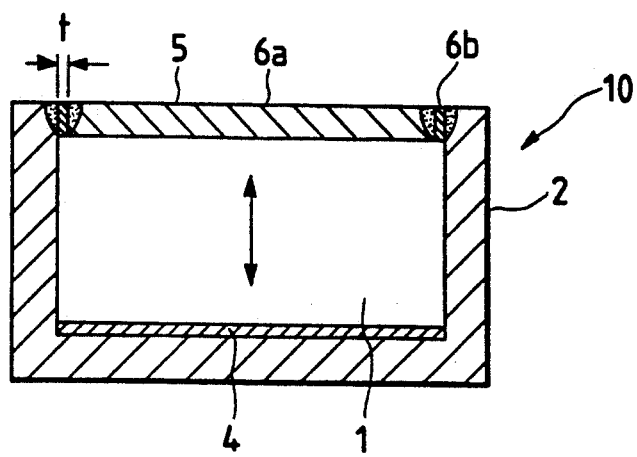
FIG. 1 is a central cross-sectional view of an embodiment of a permanent magnet assembly according to the invention.
Figure 5A:
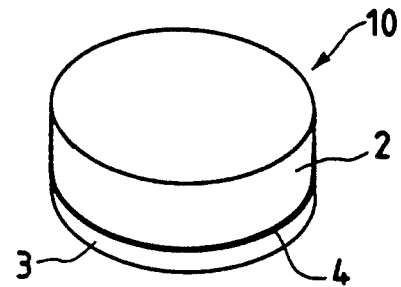
FIG. 5(a) is a perspective view of a conventional permanent magnet assembly.
Figure 5B:
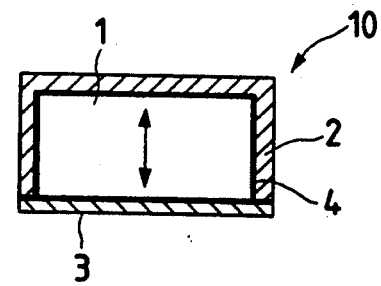
FIG. 5(b) is a diametric cross-section of the conventional assembly.

In FIG. 1, there is shown a central section view of an embodiment of a permanent magnet assembly according to the invention, in which the same parts as those shown in FIGS. 5(a) and 5(b) are designated by the same reference characters. In FIG. 1, a seal plate 5 is shown which can be formed integrally by a central seal plate portion 6a of magnetic stainless steel or the like so as to face the end face of a permanent magnet 1, and by a seal edge portion 6b of a hard chrome plated layer so as to face in the direction of the outer peripheral edges of the permanent magnet 1. The seal plate 5 is fitted into the end portions of an opening formed in a case 2 of cup-shaped configuration. The abutting portions of the seal plate 5 and case 2 are welded together by laser beam irradiation to hermetically seal the permanent magnet 1 in the case 2. In this instance, the welding should be executed in such a manner that the direction of laser beam irradiation is parallel to the axis of the case 2 and so that the laser beam is irradiated directly to the center of the width of the seal edge portion 6b.

Figure 2:
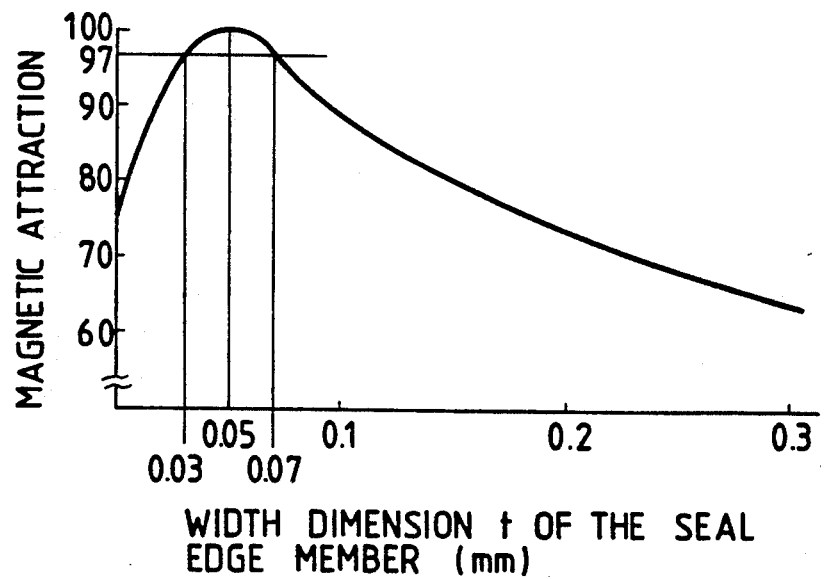
FIG. 2 is a graphical representation of a relation between the width dimension t of a seal edge portion and the magnetic attraction.

In FIG. 2, there is shown a graphical representation of the relationship between the width dimension t of the seal edge portion and the magnetic attraction, with the magnetic attraction being expressed in arbitrary units relative to a maximum value of 100. In this case, the permanent magnet 1 shown in FIG. 1 is formed of a Sm - Co system permanent magnet (H22A manufactured by Hitachi Metals) with an outside diameter of 3.2 mm and a height of 1.4 mm. The magnet is positioned in the case 2 formed of ferrite system stainless steel (magnetic) such as SUS474J1 with an outside diameter of 4.4 mm, an inside diameter of 3.4 mm, a height of 2.1 mm and an interior depth of 1.6 mm. The case is finally hermetically sealed by the seal plate 5 which has an outside diameter of 3.4 mm and a thickness of 0.20 mm. In the illustrated embodiment, the seal plate 5 is constructed by integrally combining the seal plate portion 6a formed of SUS447J1 or the like with an outside diameter of (3.4−2t) mm and a thickness of 0.20 mm and the seal edge portion 6b formed of a hard chrome-plated layer with an outside diameter of 3.4 mm, an inside diameter (3.4−2t) mm and a width of 0.20 mm in the radial direction thereof. In this embodiment, the abutting portions of the seal plate 5 and case 2 are welded and hermetically sealed by irradiation with a laser beam having a spot diameter of 0.15 to 0.20 mm in a nitrogen atmosphere.

As can be understood from FIG. 2, the magnetic attraction of the permanent magnet assembly 10 shown in FIG. 1 can be varied by changing in width dimension t of the seal edge portion 6b, and the maximum value of the magnetic attraction exists in the region of the width dimension when t=0.05 mm. That is, the magnetic attraction is increased by decreasing the width dimension t of the seal edge portion 6b. It is believed that the reason for this phenomenon is that the outside diameter of the central seal plate portion 6a shown in FIG. 1 is increased by decreasing the width dimension t. However, if the width dimension t is decreased to too small a value, then a clearance between the seal plate portion 6a and the opening end portion of the case 2 is narrowed to increase a short circuit magnetic flux and thus reduce an effective magnetic flux acting on a root surface member (not shown), with the result that the magnetic attraction is reduced. For this reason, according to the present embodiment, in order to reduce variations in the quality of the magnetic assembly, the magnetic attraction of the magnetic assembly is restricted to 97% of the maximum value.

Figure 3:
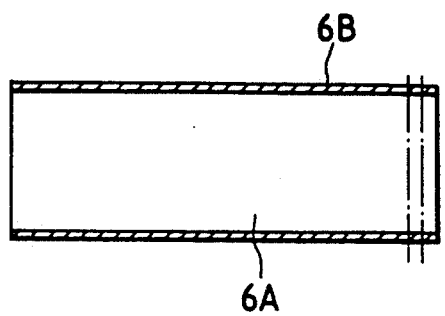
FIG. 3 is a schematic cross-sectional view to explain the preferred method for manufacturing the seal plate shown in FIG. 1.

In FIG. 3, there is shown a explanatory view of an embodiment of means for manufacturing the seal plate 5 shown in FIG. 1. In this figure, reference character 6A designates a seal plate member blank which may be formed of SUS447J1 or the like in the shape of a round rod. 6B stands for a seal edge portion blank which may be formed of a hard chrome plated layer fixed to the central seal plate portion blank 6A. Then, the thus formed seal plate member blank 6A (for example, having an outside diameter of 3.4 mm) and seal edge portion blank 6B (for example, having a thickness of 50 μm) are sliced or machined in such a manner as shown by dotted lines in FIG. 3, thereby producing the seal plate 5 shown in FIG. 1.

Figure 4:
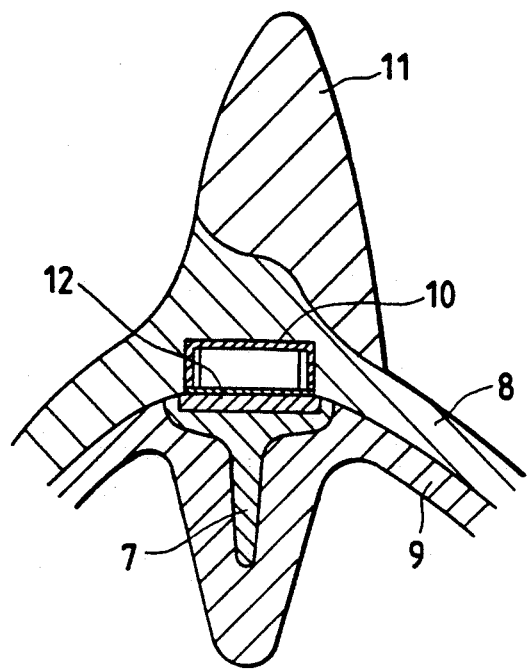
FIG. 4 is a fragmentary cross-sectional view of a false tooth fixing structure using the permanent magnet assembly according to the invention.
Figure 6:
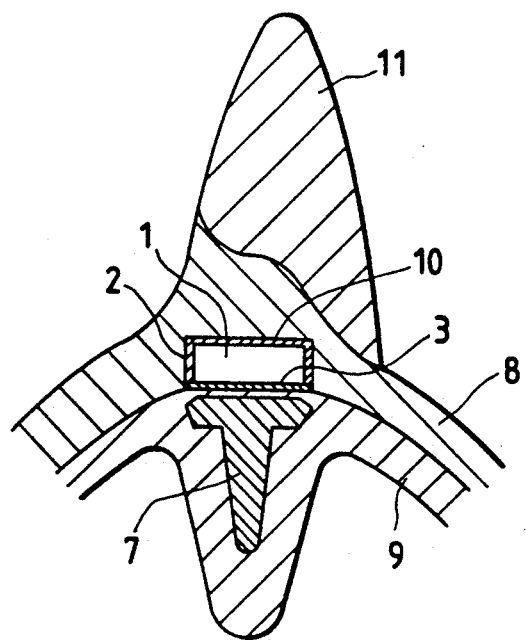
FIG. 6 is a cross-section of an exemplary false tooth fixing means using a conventional permanent magnet assembly.

In FIG. 4, there is shown a longitudinal section view of main portions of an embodiment of false tooth fixing means which uses a permanent magnet assembly according to the invention, in which the same parts as those shown in FIG. 6 are given the same reference characters. In FIG. 4, the reference character 12 designates a keeper, which may be formed of a highly permeable material such as SUS447J1 disc shape, and is embedded in the end face of a root surface member 7. Employment of this structure can further enhance the magnetic attraction to further enhance the stability of a false tooth in the mouth.

In the present embodiment, description has been given of an example in which the case 2 and seal plate portion 6a are respectively formed of SUS447J1. However, this is not limiting and these components may be formed of other corrosion resistant and non-magnetic materials. Also, the seal edge portion 6b is not limited to chrome but may be formed of other corrosion resistant and non-magnetic materials. Further, in the present embodiment, the adhesive agent 4 is used to fix the permanent magnet 1 in the case. However, other fixing means can also be employed. For example, after the permanent magnet 1 is inserted into the case 2, the seal plate 5 is disposed on the case 2 and the seal plate 5 and case 2 are laser beam welded while applying a pressure of about 1 kg/mm$^2$ to the seal plate 5, whereby the permanent magnet 1 can be fixed in the case 2 without using the adhesive agent 4.

As a result of the structural characteristics of the case 2 and cover 5 of the present invention as described above, the permanent magnet can be hermetically sealed in the case with high precision. Also, since the magnetic air gap between the permanent magnet and root surface member is very small, the magnetic attraction can be increased conveniently with an enhanced resistance to wear. Further, because the dimension of the magnetic air gap to be formed by the seal edge portion of the seal plate can be optimized, the magnetic attraction can be greatly increased. In addition, because the width dimension of the seal edge portion is small, a time required for seam welding can be reduced by substantially one half as compared to conventional structures.

The foregoing description of a preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A permanent magnet assembly for false tooth stabilization comprising:

a cup-shaped case having an opening, the case being formed of a corrosion resistant and magnetic material, a permanent magnet having opposite end faces, magnetized in the direction between the end faces thereof and positioned in the case, and a seal plate formed of a corrosion resistant material and fitted into and fixed to the opening of the case to hermetically seal the case, said seal plate comprising:

a central seal plate portion formed of a magnetic material and facing an end face of said permanent magnet, and a seal edge portion formed of a non-magnetic material, the radial width dimension of said seal edge portion being in the range of 0.03 to 0.07 mm, and at least abutting portions of said case and said seal plate being welded to each other, said seal edge portion of said seal plate facing an outer peripheral edge of an end face of said permanent magnet.

2. A permanent magnet assembly for false tooth stabilization as set forth in claim 1, wherein said seal edge portion is fixedly secured to the outer periphery of said central seal plate portion by plating.

3. A permanent magnet assembly for false tooth stabilization as set forth in claim 2, wherein the external dimensions of said central seal plate portion are smaller than the external dimensions of the end faces of said permanent magnet.

4. A permanent magnet assembly for false tooth stabilization as set forth in claim 3, wherein said permanent magnet and said case are of cylindrical configuration.

5. A permanent magnet assembly for false tooth stabilization as set forth in claim 2, wherein said permanent magnet and said case are of cylindrical configuration.

6. A permanent magnet assembly for false tooth stabilization as set forth in claim 1, wherein the external dimensions of said central seal plate portion are smaller than the external dimensions of the end faces of said permanent magnet.

7. A permanent magnet assembly for false tooth stabilization as set forth in claim 6, wherein said permanent magnet and said case are of cylindrical configuration.

8. A permanent magnet assembly for false tooth stabilization as set forth in claim 1, wherein said permanent magnet and said case are of cylindrical configuration.

* * * * *